United States Patent [19]

Kleiner

[11] Patent Number: 5,756,848
[45] Date of Patent: May 26, 1998

[54] PROCESS FOR PREPARING SECONDARY ARYLPHOSPHINE OXIDES

[75] Inventor: Hans-Jerg Kleiner, Kronberg, Germany

[73] Assignee: Hoechst Aktiengesellschaft

[21] Appl. No.: 742,293

[22] Filed: Nov. 4, 1996

[30] Foreign Application Priority Data

Nov. 6, 1995 [DE] Germany .................. 195 41 276.1

[51] Int. Cl.$^6$ ............................................. C07F 9/53
[52] U.S. Cl. ............................................. 568/14; 568/17
[58] Field of Search ................... 568/16, 17, 14; 564/14

[56] References Cited

U.S. PATENT DOCUMENTS 5,298,644  3/1994  Regnat et al. .
5,312,890  5/1994  Davis .

FOREIGN PATENT DOCUMENTS 570869  11/1993  European Pat. Off. .

OTHER PUBLICATIONS

Justus Liebigs Annalen Der Chemie, Weinheim DE, pp. 751–764; Kleiner H.J.: "Herstellung und Umsetzungen von Dimethylphosphinoxid".
Journal Of The American Chemical Society, pp. 4026–4032, Van Der Knapp T.A.: "Oxidation Reactions of Phosphaalkenes".
M.I. Kabachnik et al, Z.M. Obshch. Khim. 55, pp. 2481–2483, (1985).
Houben–Weyl, Meth. der Org. Chemie, Band XII/1, pp. 193–195, (1963).

*Primary Examiner*—Gary Geist
*Assistant Examiner*—Jean F. Vollano
*Attorney, Agent, or Firm*—Connolly & Hutz

[57] ABSTRACT

The invention relates to a process for preparing secondary arylphosphine oxides of the formula (I)

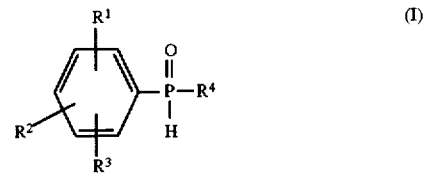

in which $R^1$ to $R^3$, independently of one another are hydrogen, halogen, trifluoromethyl, ($C_1$–$C_6$)alkyl, ($C_1$–$C_6$)alkoxy, di($C_1$–$C_6$)alkylamino, or diphenylamino and $R^4$ is ($C_1$–$C_{12}$)alkyl, cycloalkyl or aralkyl or the grouping

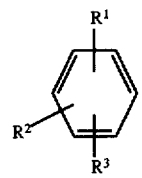

which comprises reacting arylphosphinous alkyl esters of the formula (II)

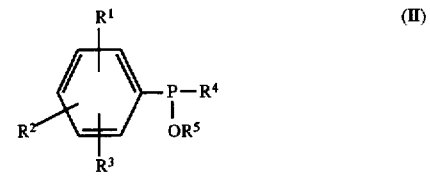

in which $R^1$, $R^2$, $R^3$ and $R^4$ have the meaning given above and $R^5$ is ($C_1$–$C_4$)alkyl, with water at elevated temperature, in a molar ratio of phosphinous ester to water of 1:1 to 1:1.5.

9 Claims, No Drawings

PROCESS FOR PREPARING SECONDARY ARYLPHOSPHINE OXIDES

The invention relates to a process for preparing secondary arylphosphine oxides.

Secondary arylphosphine oxides are valuable starting materials for preparing flame retardants, metal extraction media and tertiary phosphines as ligands. Diphenylphosphine oxide is of importance, in particular, (see, e.g., U.S. Pat. No. 5,312,890; M. I. Kabachnik et al., Zh. Obshch. Khim. 55, 2481 (1985)). The simplest form of their preparation appears to be by hydrolysis of the arylphosphinous halides (Houben-Weyl, Methoden der organischen Chemie [Methods in Organic Chemistry], Volume XII/1, 193, 1963). This succeeds in good yields in organic diluents, in order to avoid the disproportionation which is frequently to be observed. As diluent, use was made in this case of the carcinogenic carbon tetrachloride. A disadvantage in this process when it is carried out industrially is, in particular, the removal of the hydrogen halide. Complex extraction processes are necessary for this. Therefore, the hydrolysis of the arylphosphinous esters with water in the presence of organic diluents and using catalytic amounts of inorganic acids has already been proposed (M. I. Kabachnik et al., JZV. Akad. Nauk SSSR, Otdel. Khim. Nauk 9, 1584 (1962)). In this case also, obtaining pure arylphosphine oxides is technically difficult, since the inorganic acids interfere in the work-up.

There was therefore a need to develop a process which avoids the abovementioned disadvantages, can be implemented industrially without great expense and, furthermore, makes the desired products accessible both in high yield and in high purity.

This object is achieved by a process for preparing secondary arylphosphine oxides of the formula (I)

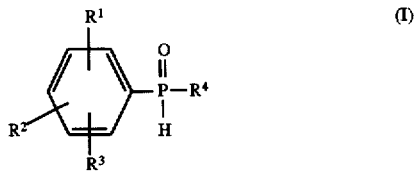

in which $R^1$ to $R^3$, independently of one another, are hydrogen, halogen, trifluoromethyl, $(C_1-C_6)$alkyl, $(C_1-C_6)$alkoxy, di$(C_1-C_6)$alkylamino, or diphenylamino and $R^4$ is $(C_1-C_{12})$alkyl, cycloalkyl or aralkyl or the grouping

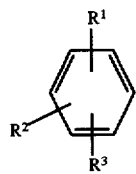

which comprises reacting arylphosphinous alkyl esters of the formula (II)

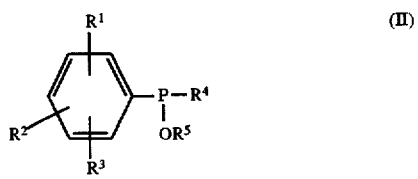

in which $R^1$, $R^2$, $R^3$ and $R^4$ have the meaning given above and $R^5$ is $(C_1-C_4)$alkyl, with water at elevated temperature, in a molar ratio of phosphinous ester to water of 1:1 to 1:1.5.

Examples of alkyl or alkoxy in the radicals $R^1$ to $R^3$ in the compounds (I)/(II) are methyl, ethyl, propyl, isopropyl and the various butyl radicals and methoxy and ethoxy. An example of dialkylamino is, in particular, dimethylamino.

Important compounds which may be prepared by the process of the invention are, for example, diphenylphosphine oxide, cyclohexylphenylphosphine oxide, isopropylphenylphosphine oxide, n-hexylphenylphosphine oxide, bis(4-fluorophenyl)phosphine oxide, (4-methoxyphenyl)phenylphosphine oxide, 4-methoxyphenyl-3-fluorophenylphosphine oxide, (4-diphenylaminophenyl)phenylphosphine oxide and bis(4-dimethylaminophenyl)phosphine oxide.

Particular importance is attached to the process for preparing compounds in which 2, in particular 3, of the radicals $R^1$ to $R^3$ are hydrogen, in particular for preparing diphenylphosphine oxide.

It must be described as surprising, that under the conditions of the invention (absence of organic diluents, elevated temperature), the known disproportionation of secondary phosphine oxides does not occur (see in this context J. B. Levy et al., Phosphorus, Sulfur and Silicon, 1993, 75, 75).

Starting materials of the formula (II) which are to be mentioned in particular are: methyl diphenylphosphinite, ethyl diphenylphosphinite, ethyl cyclohexylphenylphosphinite, ethyl isopropylphenylphosphinite, ethyl n-hexylphenylphosphinite, ethyl bis(4-fluorophenyl)phosphinite, n-propyl (4-methoxyphenyl)phenylphosphinite, ethyl 4-methoxyphenyl-3-fluorophenylphosphinite, ethyl (4-diphenylaminophenyl)phenylphosphinite and ethyl bis(4-dimethylaminophenyl)phosphinite.

The starting materials of the formula (II) are prepared by known methods, generally from the corresponding chlorophosphines by reaction with the corresponding alcohols. It is preferred to carry out the preparation in accordance with the processes of the patent applications DE File Number 19502913.5 and DE File Number 19502911.9, since particularly pure products can be prepared by these processes.

It has proved useful in many cases to heat the starting compounds of the formula (II) to 50° to 130° C., preferably 70° to 110° C., and to add water with constant stirring. The molar ratio of phosphinous ester/water is to be 1:1 to 1:1.5 in this case, in particular 1:1.05 to 1:1.2. The water is expediently added at the beginning sufficiently slowly so that the homogeneity of the reaction mixture is retained and formation of two phases does not begin. In the course of the advancing reaction, the water can then be added more rapidly. After the completion of water addition, the mixture is expediently stirred for some hours at reaction temperature. After reaction has been completed, the alcohol formed is removed by distillation in vacuo, if appropriate with excess water. The distillation residues produced represent the desired arylphosphine oxides in high purity. If appropriate, the product can be further highly purified by recrystallization or vacuum distillation.

The following examples serve to illustrate the invention.

EXAMPLE 1

1060 g (4.609 mol) of ethyl diphenylphosphinite are heated to 90° C. under a nitrogen atmosphere and 88 g of water (4.89 mol) of water are added dropwise with constant stirring in the course of 3 hours at this temperature. The mixture is then further stirred at 85° to 90° C. for 3 hours. After reaction is completed, 215 g of an ethanol/water mixture are distilled off in vacuo up to an internal temperature of 60° C. The remaining residue is poured into a dish and dried in the desiccator over phosphorus pentoxide. The melt solidifies in a crystalline form. 921 g are obtained having a melting point of 53° to 55° C. This corresponds to a yield of 99% of theory.

Distillation is possible for fine purification. (B.p.: 146° C. at 0.05 mbar)

EXAMPLE 2

36 g (0.153 mol) of ethyl cyclohexylphenylphosphinite are heated to 90° C. under a nitrogen atmosphere and 2.9 g (0.161 mol) of water are added dropwise with constant stirring in the course of 3 hours. The batch is further stirred at 85° to 90° C. for 3 hours. An ethanol/water mixture is then distilled off in vacuo up to an internal temperature of 95° C. 30.5 g of cyclohexylphenylphosphine oxide are obtained as residue. This corresponds to a yield of 96% of theory.

EXAMPLE 3

32 g (0.135 mol) of ethyl n-hexylphenylphosphinite are reacted with 2.55 g (0.142 mol) of water in the same manner as described in Example 2. 25.5 g of n-hexylphenylphosphine oxide are obtained. This corresponds to a yield of 90% of theory.

The product can be finely purified by distillation using a short-path evaporator (bath temperature 140° C. at 0.2 mbar).

It is claimed:

1. A process for preparing secondary arylphosphine oxides of the formula (I)

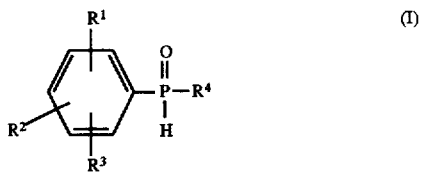

in which $R^1$ to $R^3$, independently of one another, are hydrogen, halogen, trifluoromethyl, $(C_1-C_6)$alkyl, $(C_1-C_6)$alkoxy, di$(C_1-C_6)$alkylamino, or diphenylamino and $R^4$ is $(C_1-C_{12})$alkyl, cycloalkyl or aralkyl or the grouping

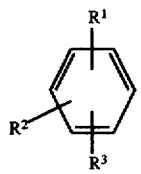

which comprises reacting arylphosphinous alkyl esters of the formula (II)

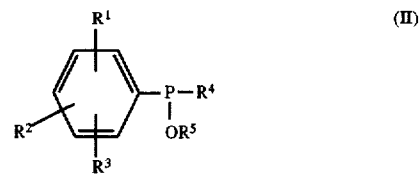

in which $R^1$, $R^2$, $R^3$ and $R^4$ have the meaning given above and $R^5$ is $(C_1-C_4)$alkyl, with water at elevated temperature in the absence of organic diluents, in a molar ratio of phosphinous ester to water of 1:1 to 1:1.5.

2. The process as claimed in claim 1, wherein 2 of the radicals $R^1$ to $R^3$ are hydrogen.

3. The process as claimed in claim 1, wherein formula (I) is diphenylphosphine oxide, cyclohexylphenylphosphine oxide, isopropylphenylphosphine oxide, n-hexylphenylphosphine oxide, bis(4-fluorophenyl) phosphine oxide, (4-methoxyphenyl)phenylphosphine oxide, 4-methoxyphenyl-3-fluorophenylphosphine oxide, (4-diphenylaminophenyl)phenylphosphine oxide or bis(4-dimethylaminophenyl)phosphine oxide.

4. The process as claimed in claim 1, wherein the starting materials of the formula (II) are heated to 50° to 130° C., and water is added with stirring.

5. The process as claimed in claim 1, wherein the molar ratio of phosphinous ester to water is 1:1.05 to 1:1.2.

6. The process as claimed in claim 1, wherein, as starting material of the formula (II), use is made of methyl diphenylphosphinite, ethyl diphenylphosphinite, ethyl cyclohexylphenylphosphinite, ethyl isopropylphenylphosphinite, ethyl n-hexylphenylphosphinite, ethyl bis(4-fluorophenyl) phosphinite, n-propyl (4-methoxyphenyl) phenylphosphinite, ethyl 4-methoxyphenyl-3-fluorophenylphosphinite, ethyl (4-diphenylaminophenyl) phenylphosphinite or ethyl bis(4-dimethylaminophenyl) phosphinite.

7. The process as claimed in claim 1, wherein 3 of the radicals $R^1$ to $R^3$ are hydrogen.

8. The process as claimed in claim 1, wherein formula (I) is diphenylphosphine oxide.

9. The process as claimed in claim 1, wherein the starting materials of the formula (II) are heated to 70° to 110° C. and water is added with stirring.

* * * * *